(12) United States Patent
DeFalco et al.

(10) Patent No.: US 10,620,219 B2
(45) Date of Patent: Apr. 14, 2020

(54) USE OF NANOEXPRESSION TO INTERROGATE ANTIBODY REPERTOIRES

(71) Applicant: ATRECA, INC., San Carlos, CA (US)

(72) Inventors: Jeff DeFalco, Foster City, CA (US); Daniel Emerling, San Carlos, CA (US); Shaun Lippow, San Carlos, CA (US); Sean Carroll, San Carlos, CA (US); Wayne Volkmuth, Foster City, CA (US); Norm Greenberg, San Carlos, CA (US); Tito Serafini, Belmont, CA (US)

(73) Assignee: ATRECA, INC., S. San Francisco, CA (US)

( * ) Notice: Subject to any disclaimer, the term of this patent is extended or adjusted under 35 U.S.C. 154(b) by 113 days.

(21) Appl. No.: 15/840,142

(22) Filed: Dec. 13, 2017

(65) Prior Publication Data

US 2018/0100864 A1 Apr. 12, 2018

Related U.S. Application Data

(62) Division of application No. 14/319,489, filed on Jun. 30, 2014, now abandoned.

(60) Provisional application No. 61/842,561, filed on Jul. 3, 2013.

(51) Int. Cl.
*C40B 30/04* (2006.01)
*G01N 33/68* (2006.01)

(52) U.S. Cl.
CPC .......... *G01N 33/6854* (2013.01); *C40B 30/04* (2013.01)

(58) Field of Classification Search
None
See application file for complete search history.

(56) References Cited

U.S. PATENT DOCUMENTS

2012/0015829 A1 1/2012 Wiley
2012/0077713 A1 3/2012 Enzelberger

*Primary Examiner* — Christian C Boesen
(74) *Attorney, Agent, or Firm* — Kilpatrick Townsend & Stockton LLP (57) ABSTRACT

Disclosed herein are methods and compositions for using nanoexpression to interrogate antigen specificity within antibody repertoires. Also disclosed herein is an antibody display system composition comprising one or more recombinant nucleic acid sequences comprising a first nucleic acid sequence encoding a heavy chain variable region sequence or fragment thereof operatively linked to a first identification region sequence and a second nucleic acid sequence encoding a light chain variable region sequence or fragment thereof operatively linked to a second identification region sequence.

7 Claims, 2 Drawing Sheets

USE OF NANOEXPRESSION TO INTERROGATE ANTIBODY REPERTOIRES

CROSS REFERENCE TO RELATED APPLICATIONS

This application is a divisional of U.S. patent application Ser. No. 14/319,489, filed Jun. 30, 2014, which claims priority to U.S. Provisional Application No. 61/842,561, filed Jul. 3, 2013, all of which are herein incorporated by reference, in their entirety, for all purposes.

BACKGROUND

Current methods allow the creation of antibody repertoires of paired heavy and light chain sequences having identification regions (i.e., barcodes) and originating from single cells. See, e.g., PCT/US2012/000221 (filed Apr. 27, 2012) and PCT/US2012/053698 (filed Sep. 4, 2012), each of which is herein incorporated by reference in its entirety for all purposes. Typically phylogenetic trees generated using these methods can represent over a thousand paired antibodies with considerable diversity. Even where source cells are antigen-sorted it is not necessarily clear which members of the repertoire are capable of interacting with a given antigen, to which epitopes within an antigen, and with what degree of affinity. One approach toward interrogating antibody binding characteristics for individual members within the repertoire is to "cherry-pick" specific members and have the antibodies expressed in a variety of eukaryotic expression systems. While this method can produce functional antibodies it is generally considered inefficient for several reasons: First, antigen specificity typically cannot always be determined a priori from a protein sequence; second, large numbers of antibodies would typically need to be tested to ensure adequate coverage of the repertoire; third, in-vitro production of individual antibodies can be time consuming and expensive, particularly considering the number of antibodies that would usually need to be tested.

Typical antibody display strategies include combinatorial libraries in which variable domains from heavy and light chains from unpaired cDNA repertoires are paired in a random fashion. This blind, shotgun approach to H+L pairing uses the construction of libraries with complexities that can exceed $10^9$ and pose technical challenges when trying to reach the maximum efficiencies necessary to create such a library.

SUMMARY

Disclosed herein are methods and compositions for using nanoexpression to interrogate antigen specificity within antibody repertoires.

Antibody display technologies, including phage display, include libraries representing randomly paired heavy and light chain cDNA typically derived from pools of polyclonal B-cells. Using phage display libraries as an example, cDNA encoding the heavy and light chains are integrated into the phage genome and are produced as a fusion protein presented on the surface of the phage. Since the antibody domain of the fusion protein is typically functional, one can apply billions of phage to an antigen target, wash away non-binders and isolate and characterize those clones that are capable of binding. This positive selection strategy permits the identification of positive clones that are only a minor fraction of the entire repertoire screened. Furthermore, using a fully sequenced and barcoded repertoire as starting material offers several advantages including: a) tailored primer design; b) providing a metric to measure library complexity at each stage of construction; c) the creation of sub-libraries based on selected heavy and light chain PCR product pairing, increasing the frequency of native H+L pairings relative to non-native pairings; and d) creation of display libraries consisting of specifically paired H+L chain clones. The ability to either enrich for or restrict the display library to native pairs reduces the complexity of the library, decreasing background "noise" as well as the number of phage particles that must be selected. Thus, the combination of antibody display technologies with a fully sequenced and barcoded repertoire of antibodies provides the ability to interrogate and annotate antigen specificity within the antibody repertoire.

Disclosed herein is an antibody display system composition comprising one or more recombinant nucleic acid sequences comprising a first nucleic acid sequence encoding a heavy chain variable region sequence or fragment thereof operatively linked to a first identification region sequence and a second nucleic acid sequence encoding a light chain variable region sequence or fragment thereof operatively linked to a second identification region sequence.

In some aspects, the first and second identification region sequences are distinct. In some aspects, the first and second identification region sequences are identical. In some aspects, the one or more recombinant nucleic acid sequences comprises a Fab sequence. In some aspects, the one or more recombinant nucleic acid sequences comprises a scFv sequence.

In some aspects, the antibody display system composition is a phagemid. In some aspects, the antibody display system composition is a ribosome, cell, mRNA, mammalian cell, bacteria, or yeast cell.

Also disclosed herein is an antibody display system library comprising a plurality of the antibody display system compositions disclosed herein.

Also disclosed herein is a method of annotating an antibody display system library with binding data, comprising: obtaining a library disclosed herein bound to an antigen of interest, wherein the sequences used to construct the library were known; determining a dataset comprising binding data and sequence data for the library; and annotating the library with the data of the dataset using the sequence data and the known sequences used to construct the library.

Also disclosed herein is a method of annotating an antibody repertoire, comprising: obtaining a first dataset, wherein the first dataset comprises sequence data for a plurality of heavy and light chain antibody sequence pairs each from a distinct single sample, wherein each sequence of each pair is operatively linked to an identification region sequence, and wherein each identification region sequence is unique relative to the other identification region sequences within the plurality; creating an antibody display system using the dataset, wherein the antibody display system comprises a plurality of components; binding the antibody display system to an antigen; determining a second dataset comprising binding data and sequence data based on the binding step; and annotating the sequence data of the first dataset with the data of the second dataset.

In some aspects, the antibody display system is a library disclosed herein. In some aspects, the single sample is a single B cell.

In some aspects, the binding data is affinity data. In some aspects, the binding data is antigen-specificity data. In some aspects, the binding data is determined using an ELISA assay. In some aspects, the sequence data of the second dataset is determined using sequencing. In some aspects, the sequence data of the second dataset is determined using next generation sequencing (NGS).

In some aspects, the antigen is a recombinant protein, a cell, a subcellular fraction, a bacterium, fungi, protozoa, or a tissue.

In some aspects, the sequence data of the second dataset comprises sequence data for a plurality of heavy and light chain antibody sequences, wherein each sequence is operatively linked to an identification region sequence. In some aspects, the sequence data of the first dataset is annotated with the binding data of the second dataset by comparison of the identification region sequence data of the first dataset to the identification region sequence data of the second dataset.

In some aspects, a method disclosed herein further comprises repeating the binding and determining steps.

In some aspects, the determining step comprises determining sequence data for bound antibody display system components only. In some aspects, the determining step comprises determining sequence data for both bound and unbound antibody display system components.

In some aspects, a method disclosed herein further comprises selecting one or more sequences from the first dataset for further analysis based on the annotation step.

In some aspects, a method disclosed herein further comprises sequencing the antibody display system.

BRIEF DESCRIPTION OF THE SEVERAL VIEWS OF THE DRAWINGS

These and other features, aspects, and advantages will become better understood with regard to the following description, and accompanying drawings, where.

DETAILED DESCRIPTION

Compositions

Polynucleotides

In some aspects, a composition can include a polynucleotide. The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, can be modified. Typical modifications include methylation, biotinylation, and other art-known modifications. In addition, a polynucleotide can be single-stranded or double-stranded and, where desired, linked to a detectable moiety. In some aspects, a polynucleotide can include hybrid molecules, e.g., comprising DNA and RNA.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in nucleotide sequences by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods described herein.

As used herein, and unless otherwise indicated, the term "complementary," when used to describe a first nucleotide sequence in relation to a second nucleotide sequence, refers to the ability of a polynucleotide comprising the first nucleotide sequence to hybridize and form a duplex structure under certain conditions with a polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Complementary sequences include base-pairing of a region of a polynucleotide comprising a first nucleotide sequence to a region of a polynucleotide comprising a second nucleotide sequence over the length or a portion of the length of one or both nucleotide sequences. Such sequences can be referred to as "complementary" with respect to each other herein. However, where a first sequence is referred to as "substantially complementary" with respect to a second sequence herein, the two sequences can be complementary, or they may include one or more, but generally not more than about 5, 4, 3, or 2 mismatched base pairs within regions that are base-paired. For two sequences with mismatched base pairs, the sequences will be considered "substantially complementary" as long as the two nucleotide sequences bind to each other via base-pairing.

"Complementary" sequences, as used herein, may also include, or be formed entirely from, non-Watson-Crick base pairs and/or base pairs formed from non-natural and modified nucleotides, in as far as the above embodiments with respect to their ability to hybridize are fulfilled. Such non-Watson-Crick base pairs includes, but are not limited to, G:U Wobble or Hoogstein base pairing.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information web-site.

Identical sequences include 100% identity of a polynucleotide comprising a first nucleotide sequence to a polynucleotide comprising a second nucleotide sequence over the entire length of one or both nucleotide sequences. Such sequences can be referred to as "fully identical" with respect to each other herein. However, in some aspects, where a first sequence is referred to as "substantially identical" with respect to a second sequence herein, the two sequences can be fully complementary, or they may have one or more, but generally not more than about 5, 4, 3, or 2 mismatched nucleotides upon alignment. In some aspects, where a first sequence is referred to as "substantially identical" with respect to a second sequence herein, the two sequences can be fully complementary, or they may be about 50, 60, 70, 80, 81, 82, 83, 84, 85, 86, 87, 88, 89, 90, 91, 92, 93, 94, 95, 96, 97, 98, or 99% identical to each other.

Where a first sequence is referred to as "distinct" with respect to the identity of a second sequence herein, the two sequences have at least one or more mismatched nucleotides upon alignment. In some aspects, distinct sequences can have 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more mismatched nucleotides upon alignment. In some aspects, distinct sequences can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 81, 82, 83, 84, 85, 86, 87, 88, 89, 90, 91, 92, 93, 94, 95, 96, 97, 98, 99, or less than 100% identical to each other. In some aspects, where a first sequence is referred to as "distinct" with respect to a second sequence herein, the two sequences can have substantially or fully identical sequences, but instead differ from one another based upon differing patterns of modification within the sequences. Such modifications are generally known in the art, e.g., methylation.

In some aspects, a polynucleotide can be present in a library of polynucleotides. In some aspects, a polynucleotide library can include a plurality of polynucleotides. In some aspects, each polynucleotide in the plurality of polynucleotides can be derived from a single sample. In some aspects, a single sample can include a single cell such as a B cell.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

The term "messenger RNA" or "mRNA" refers to an RNA that is without introns and that can be translated into a polypeptide.

The term "cDNA" refers to a DNA that is complementary or identical to an mRNA, in either single stranded or double stranded form.

The term "amplicon" refers to the amplified product of a nucleic acid amplification reaction, e.g., RT-PCR.

The term "hybridize" refers to a sequence specific non-covalent binding interaction with a complementary nucleic acid. Hybridization may occur to all or a portion of a nucleic acid sequence. Those skilled in the art will recognize that the stability of a nucleic acid duplex, or hybrids, can be determined by the Tm. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

As used herein, "region" refers to a contiguous portion of the nucleotide sequence of a polynucleotide. Examples of regions are described herein an include identification regions, sample identification regions, plate identification regions, adapter regions, and the like. In some aspects, a polynucleotide can include one or more regions. In some aspects, a polynucleotide can include less than 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more regions. In some aspects, regions can be coupled. In some aspects, regions can be operatively coupled. In some aspects, regions can be physically coupled.

As used herein, "variable region" refers to a variable nucleotide sequence that arises from a recombination event, for example, it can include a V, J, and/or D region of an immunoglobulin or T cell receptor sequence isolated from a T cell or B cell of interest, such as an activated T cell or an activated B cell.

As used herein "B cell variable immunoglobulin region" refers to a variable immunoglobulin nucleotide sequence isolated from a B cell. For example, a variable immunoglobulin sequence can include a V, J, and/or D region of an immunoglobulin sequence isolated from a B cell of interest such as a memory B cell, an activated B cell, or plasmablast.

As used herein "identification region" refers to a nucleotide sequence label (e.g., a unique barcode sequence) that can be coupled to at least one nucleotide sequence for, e.g., later identification of the at least one nucleotide sequence.

As used herein "immunoglobulin region" refers to a contiguous portion of nucleotide sequence from one or both chains (heavy and light) of an antibody.

As used herein "adapter region" refers to a linker that couples a first nucleotide sequence to a second nucleotide sequence. In some aspects, an adapter region can include a contiguous portion of nucleotide sequence that acts as a linker. For example, an adapter region can have the sequence GGG and couples a first sequence to a second sequence via binding between GGG and CCC.

In some aspects, a polynucleotide can include a cDNA region. In some aspects, a polynucleotide can include a sample identification-adapter region. In some aspects, a polynucleotide can include a sample identification region. In some aspects, a polynucleotide can include an adapter region. In some aspects, a polynucleotide can include a universal primer region. In some aspects, a polynucleotide can include an amplicon region. In some aspects, a polynucleotide can include a plate identification region. In some aspects, a polynucleotide can include a first plate identification region. In some aspects, a polynucleotide can include a second plate identification region. In some aspects, a polynucleotide can include a restriction site region. In some aspects, a polynucleotide can include a first restriction site region. In some aspects, a polynucleotide can include a second restriction site region. In some aspects, a polynucleotide can include a sequencing region. In some aspects, a polynucleotide can include a first sequencing region. In some aspects, a polynucleotide can include a second sequencing region.

In some aspects, a polynucleotide can include a plurality of any region described herein. For example, a polynucleotide can include a first sample identification region and a second sample identification region. In some aspects, the first sample identification region and the second sample identification region are identical or substantially identical. In some aspects, the first sample identification region and the second sample identification region are distinct. In some aspects, an identification region is coupled to a variable immunoglobulin region.

In some aspects the sequence of a region will be at least long enough to serve as a target sequence for a primer or a probe in a PCR reaction. In some aspects, a region can be 1 to greater than 5000 base pairs in length. For example, a region can be from 1-10,000 nucleotides in length, e.g., 2-30 nucleotides in length, including all sub-ranges therebetween. As non-limiting examples, a region can be from 1-30 nucleotides, 1-26 nucleotides, 1-23 nucleotides, 1-22 nucleotides, 1-21 nucleotides, 1-20 nucleotides, 1-19 nucleotides, 1-18 nucleotides, 1-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides. In some aspects, a region can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more nucleotides in length. In some aspects, a region can be less than 50, 50-100, 100-200, 200-300, 300-400, 400-500, 500-600, 600-700, 700-800, 800-900, 900-1000, or greater than 1000 nucleotides in length. In some aspects, a region can be less than 1000, 1000-2000, 2000-3000, 3000-4000, 4000-5000, 5000-6000, 6000-7000, 7000-8000, 8000-9000, 9000-10000, or greater than 10000 nucleotides in length. In some aspects, a region can include at least two nucleotides, at least 3, at least 4, at least 5, at least 6, at least 7, at least 8, at least 9, at least 10, at least 15, at least 20 or more nucleotides of a polynucleotide disclosed herein.

The term "sample" can include RNA, DNA, a single cell or multiple cells or fragments of cells or an aliquot of body fluid, taken from a subject (e.g., a mammalian subject, an animal subject, a human subject, or a non-human animal subject). Samples can be selected by one of skill in the art using any means now known or later discovered including centrifugation, venipuncture, blood draw, excretion, swabbing, ejaculation, massage, biopsy, needle aspirate, lavage sample, scraping, surgical incision, laser capture microdissection, gradient separation, or intervention or other means known in the art. Samples can also be selected by one of skill in the art using one or more markers known to be associated with a sample of interest. Samples can also be selected using methods known in the art such as cell sorting and FACS. Further examples of sample selection methods are described in the Examples section below.

In some aspects a polynucleotide can be derived from or associated with a single sample. In some aspects a region can be derived from or associated with a single sample. In some aspects, a cDNA region can be derived from or associated with a single sample. In some aspects, an amplicon region can be derived from or associated with a single sample. A "single sample" includes a sample comprising polynucleotides that is taken from a single source. In some aspects, a single source includes a sample taken at a particular time point or at a particular location, e.g., in a subject or flask of cells or plate of cells. In some aspects, a first single sample is taken from a first subject at a first time point and a second single sample is taken from the first subject at a second time point that is distinct from the first time point. In some aspects, a first single sample is taken from a first subject at a first location and a second sample is taken from the first subject at a second location that is distinct from the first location. In some aspects, a first single sample is taken from a first subject at a time point and a second single sample is taken from a second subject at a time point. In some aspects, a first single sample is taken from a first subject at a location and a second sample is taken from a second subject at a location. In one embodiment, a sample comprises polynucleotides that include mRNA derived from one or more B cells. In another embodiment, a sample comprises polynucleotides including cDNA derived from one or more B cells. In another embodiment, a single sample comprises mRNA derived from one or more B cells sorted into a single well of a 96-well or 384-well plate. Samples are generally derived from a prokaryotic cell(s) (e.g., a bacterial cell(s)), a eukaryotic cell(s) (e.g., a mammalian and yeast cell(s)), or other sources of genetic material such as a virus or phage. The term "mammal" or "mammalian" as used herein includes both humans and non-humans and include but is not limited to humans, non-human primates, canines, felines, murines, bovines, equines, and porcines. In some aspects, the methods of the invention are applied to single samples in a plate with at least 96 wells, at least 384 wells, at least 1536 wells, or more wells. In further aspects, the methods of the invention are applied to single samples in at least one, two, three, four, five, six, seven, eight, ten, fifteen, twenty, thirty or more plates with at least 96 wells each.

In some aspects a 5' adaptor region sequence and/or a sample identification region are added to all cDNAs from a single sample, e.g., during RT and not just to Ig genes. In some aspects, 3' gene specific primers (GSPs) can be used to amplify any expressed gene in the single sample. In some aspects, genes are amplified that have a 5' variable region, e.g., T cell receptors and B cell receptors without needing multiple degenerate 5' primers to amplify the gene(s) of interest. GSPs can include primers specific for IgG, IgM, IgD, IgA, IgE, TCR chains, and other genes of interest.

In some aspects, multiple rounds of PCR can also be performed, e.g., using nested GSPs. For such nested GSPs, the GSP for the second round of PCR hybridizes to its target gene sequence at a position 5' along that sequence relative to the position hybridized to by the GSP used in the first round of PCR.

In some aspects, cDNA region or an amplicon region can include a DNA polynucleotide. In some aspects, cDNA region or an amplicon region can include a cDNA polynucleotide. In some aspects, cDNA region or an amplicon region can include an RNA polynucleotide hybridized to a DNA polynucleotide. In some aspects, cDNA region or an amplicon region can include an mRNA polynucleotide hybridized to a cDNA polynucleotide.

In some aspects, a universal primer region is not fully complementary to any human exon. In some aspects, a universal primer region is not fully complementary to any expressed human gene. In some aspects, a universal primer region has minimal secondary structure.

In some aspects, an amplicon region comprises an immunoglobulin heavy chain amplicon sequence. In some aspects, an amplicon region comprises an immunoglobulin light chain amplicon sequence. In some aspects, an amplicon region comprises a T cell receptor alpha amplicon sequence. In some aspects, an amplicon region comprises a T cell receptor beta amplicon sequence.

In some aspects, a polynucleotide is present in a library of polynucleotides and can be differentiated from other polynucleotides present in the library based on a region of the polynucleotide.

In some aspects, the sequence of the sample identification region of each polynucleotide in a library derived from a first single sample is distinct from the sequence of the sample identification region of the other polynucleotides in the library derived from one or more samples distinct from the first single sample. In some aspects, the sequence of the sample identification region of each polynucleotide in a library derived from a first single sample differs by at least 1 nucleotide from the sequence of the sample identification region of the other polynucleotides in the library derived from one or more samples distinct from the first single sample. In some aspects, the sequence of the sample identification region of each polynucleotide in a library derived from a first single sample differs by at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides from the sequence of the sample identification region of the other polynucleotides in the library derived from one or more samples distinct from the first single sample. In some aspects, the sequence of the sample identification region of each polynucleotide in a library derived from a first single sample can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 81, 82, 83, 84, 85, 86, 87, 88, 89, 90, 91, 92, 93, 94, 95, 96, 97, 98, 99, or less than 100% identical to the sequence of the sample identification region of the other polynucleotides in the library derived from one or more samples distinct from the first single sample. In some aspects, the sequence of the sample identification region of each polynucleotide in a library derived from a first single sample is less than 100% identical to the sequence of the sample identification region of the other polynucleotides in the library derived from one or more samples distinct from the first single sample. In some aspects, a sample-identification region acts as a digital barcode on all 1$^{st}$ strand cDNA reverse transcribed from a single sample. In some aspects, the sample identification region is at least 1 nucleotide in length. In some aspects, a sample-identification region can comprise at least 3 nucleotides, and sample-identification regions can differ from each other by at least 1 nucleotide. In one embodiment, sample-identification regions are 3-15 nucleotides in length and differ from each other by at least 1 nucleotide. In some aspects, sample-identification regions can comprise at least 64 variants (using sample-identification regions 3 nucleotides in length with each sample-ID differing from each other by at least 1 nucleotide), or in some aspects larger numbers of variants. In some aspects, the sequence attached 3' to the sample-identification region can be an adapter region comprising at least 1 G. In a preferred embodiment, the sequence attached 3' to the sample-identification region can be an adapter region comprising at least 2 G's. In one embodiment, a sequence attached to the 5' end of a sample-identification region is a universal primer sequence that can be used during PCR amplification to avoid the need for the subsequent addition of a 5' universal primer sequence (by ligation or another method) or the use of multiple degenerate 5' primers to amplify genes with variable 5' regions. Examples of sample identification regions are shown in Tables 2 and 8.

In some aspects, the sequence of the first plate identification region of each polynucleotide in a library derived from a first set of single samples is distinct from the sequence of the first plate identification region of the other polynucleotides in the library derived from one or more single sample sets distinct from the first set of single samples. In some aspects, the sequence of the first plate identification region of each polynucleotide in a library derived from the first set of single samples differs by at least 1 nucleotide from the sequence of the first plate identification region of the other polynucleotides in the library derived from one or more single sample sets distinct from the first set of single samples. In some aspects, the sequence of the first plate identification region of each polynucleotide in a library derived from the first set of single samples differs by at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides from the sequence of the first plate identification region of the other polynucleotides in the library derived from one or more single sample sets distinct from the first set of single samples. In some aspects, the sequence of the first plate identification region of each polynucleotide in a library derived from the first set of single samples can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 81, 82, 83, 84, 85, 86, 87, 88, 89, 90, 91, 92, 93, 94, 95, 96, 97, 98, 99, or less than 100% identical to sequence of the first plate identification region of the other polynucleotides in the library derived from one or more single sample sets distinct from the first set of single samples. In some aspects, the sequence of the first plate identification region of each polynucleotide in a library derived from the first set of single samples is less than 100% identical to sequence of the first plate identification region of the other polynucleotides in the library derived from one or more single sample sets distinct from the first set of single samples. Examples of first plate identification regions are shown in Tables 3 and 7.

In some aspects, the sequence of the second plate identification region of each polynucleotide in a library derived from a first set of single samples is distinct from the sequence of the second plate identification region of the other polynucleotides in the library derived from one or more single sample sets distinct from the first set of single samples. In some aspects, the sequence of the second plate identification region of each polynucleotide in a library derived from the first set of single samples differs by at least 1 nucleotide from the sequence of the second plate identification region of the other polynucleotides in the library derived from one or more single sample sets distinct from the first set of single samples. In some aspects, the sequence of the second plate identification region of each polynucleotide in a library derived from the first set of single samples differs by at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides from the sequence of the second plate identification region of the other polynucleotides in the library derived from one or more single sample sets distinct from the first set of single samples. In some aspects, the sequence of the second plate identification region is identical to the sequence of the first plate identification region on a polynucleotide. In some aspects, the sequence of the second plate identification region of each polynucleotide in a library derived from the first set of single samples can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 81, 82, 83, 84, 85, 86, 87, 88, 89, 90, 91, 92, 93, 94, 95, 96, 97, 98, 99, or less than 100% identical to sequence of the second plate identification region of the other polynucleotides in the library derived from one or more single sample sets distinct from the first set of single samples. In some aspects, the sequence of the second plate identification region of each polynucleotide in a library derived from the first set of single samples is less than 100% identical to sequence of the second plate identification region of the other polynucleotides in the library derived from one or more single sample sets distinct from the first set of single samples. Examples of second plate identification regions are shown in Tables 3 and 7.

In some aspects, a plate-identification region (e.g., a first plate identification region or a second plate identification region) can comprise at least 2 nucleotides, and plate-identification regions differ from each other by at least 1 nucleotide. In one embodiment, plate-identification regions are 2-10 nucleotides in length and differ from each other by at least 1 nucleotide. In some aspects, use of plate-identification regions is found in only some embodiments, as the use of a larger number of different sample-identification regions (one per single sample to be analyzed) can eliminate the need for plate-identification regions. In some aspects, plate-identification regions are used to reduce the number of unique oligonucleotides containing a sample-identification region that need to be synthesized.

In some aspects, a polynucleotide includes one or more adapter regions. In some aspects, an adapter region includes one or more G's. In some aspects, an adapter region includes 2, 3, 4, 5, 6, 7, 8, 9, 10 or more G's. In some aspects, adapter regions are attached to the 3' ends of cDNAs using the template switching property of MMLV H⁻ reverse transcriptases. Different methods to attach adaptor regions exist, including but not limited to, doing PCR with primers with 5' flanking adaptor region sequences, sticky and blunt end ligations, template-switching-mediated addition of nucleotides, or other methods to covalently attach nucleotides to the 5' end, to the 3' end, or to the 5' and 3' ends of the polynucleotides. These methods can employ properties of enzymes commonly used in molecular biology. PCR can use, e.g., thermophilic DNA polymerase. Sticky ends that are complementary or substantially complementary are created through either cutting dsDNA with restriction enzymes that leave overhanging ends or through 3' tailing activities of enzymes such as TdT (terminal transferase). Sticky and blunt ends can then be ligated with a complementary adaptor region using ligases such as T4 ligase. Template-switching utilizes the 3' tailing activity of MMLV H⁻ reverse transcriptase to add one or more cytosines (C's) to the 3' end of cDNAs and its ability to switch template from mRNA to an adaptor region with complementary G's. In some aspects, a cDNA includes 1, 2, 3, 4, 5, 6, 7, 8, 9, 10 or more C's on its 3' end.

In some aspects, a polynucleotide includes one or more restriction site regions. Restriction site regions include one or more restriction sites. Restrictions sites can include: NheI, XhoI, BstBI, EcoRI, SacII, BbvCI, PspXI, AgeI, ApaI, KpnI, Acc65I, XmaI, BstEII, DraIII, PacI, FseI, AsiSI, and AscI. In some aspects, any rare 8-cutter enzyme restriction site can be used.

In some aspects, one or more regions of a polynucleotide described herein can be operatively coupled to one or more other regions of the polynucleotide. In some aspects, two or more distinct regions of a single polynucleotide can be operatively coupled. For example, a universal primer region can be operatively coupled to an adapter region. In some aspects two or more regions can be operatively coupled together that are substantially identical to each other in sequence or identical in description. For example, a first sample identification region can be operatively coupled to a second sample identification region. In some aspects, the sequences of the first sample identification region and the second sample identification region are identical or substantially identical. In some aspects, the sequences of the first sample identification region and the second sample identification region are different or distinct.

In some aspects, one or more regions of a polynucleotide described herein can be coupled to one or more other regions of the polynucleotide. In some aspects, two or more distinct regions of a single polynucleotide can be coupled. For example, a universal primer region can be coupled to an adapter region. In some aspects two or more regions can be coupled together that are substantially identical to each other in sequence or identical in description. For example, a first sample identification region can be coupled to a second sample identification region. In some aspects, the sequences of the first sample identification region and the second sample identification region are identical or substantially identical. In some aspects, the sequences of the first sample identification region and the second sample identification region are different or distinct.

In some aspects, a polynucleotide includes the sequence 5'-A-B-3', wherein A is a sample identification region, and wherein B is an adapter region. In some aspects, a polynucleotide includes the sequence 5'-A-B-C-3', wherein A is a universal primer region, wherein B is a sample identification region, and wherein C is an adapter region. In some aspects, a polynucleotide includes the sequence 5'-A-B-C-3', wherein A is a sample identification region, wherein B is an adapter region, and wherein C is an amplicon region derived from a single sample. In some aspects, a polynucleotide includes the sequence 5'-A-B-C-D-3', wherein A is a universal primer region, wherein B is a sample identification region, wherein C is an adapter region, and wherein D is an amplicon region derived from a single sample. In some aspects, a polynucleotide includes the sequence 5'-A-B-C-D-E-3', wherein A is a plate identification region, wherein B is a universal primer region, wherein C is a sample identification region, wherein D is an adapter region, and wherein E is an amplicon region derived from a single sample. In some aspects, a polynucleotide includes the sequence 5'-A-B-C-D-E-F-3', wherein A is a first restriction site region, wherein B is a universal primer region, wherein C is a sample identification region, wherein D is an adapter region, wherein E is an amplicon region derived from a single sample, and wherein F is a second restriction site region.

In some aspects, the regions of each of the above sequences can be rearranged in a different order, e.g., 5'-C-A-D-B-3' or 5'-E-A-C-B-D-F-3' or 5'-B-A-3'. In some aspects, one or more regions of the above sequences can be deleted, e.g., 5'-A-D-3' or 5'-B-C-3'. In some aspects, one or more additional regions can be added to the above sequences, e.g., 5'-A-$A_2$-B-3' or 5'-A-B-C-D-E-F-G-3'. In such examples the one or more additional regions can be any region disclosed herein or equivalents thereof. In some aspects, one or more regions of the sequences above can be modified, e.g., methylated.

In some aspects, a polynucleotide can include an adapter molecule. In some aspects, a polynucleotide adapter molecule can include a universal primer region, a sample identification region, and an adapter region, wherein the 3' end of the universal primer region is coupled to the 5' end of the sample identification region, and wherein the 3' end of the sample identification region is coupled to the 5' end of the adapter region. In some aspects, an adapter molecule includes a polynucleotide comprising at least 2 nucleotides that bind to C's added by a reverse transcriptase at the 3' end of a 1st strand cDNA. In some aspects, an adapter molecule includes a deoxyribose polynucleotide comprising 3-6 G's (DNA G's). In another embodiment, an adapter molecule includes a ribose polynucleotide consisting of 3-6 G's (RNA G's). In other embodiments, the adapter molecule can utilize nucleotide analogues, such locked nucleic acids (LNAs), e.g., LNA G's. In other embodiments, the nucleotide base may also be a universal or degenerate base such as 5-nitroindole and 3-nitropyrrole that can base-pair to C's as well as other nucleotides, in any combination.

In some aspects, a polynucleotide can include a primer or a probe. In some aspects, a primer can include a universal primer region and a plate identification region, and wherein the 3' end of the plate identification region is coupled to the 5' end of the universal primer region.

In some aspects, a composition can include a polynucleotide composition library. In some aspects, a polynucleotide composition library includes a plurality of polynucleotide compositions. In some aspects each composition is present in a separate container. In some aspects, a container can be a test tube. In some aspects, a container can be a well in a plate. In some aspects, a container can be a well in a 96-well plate. In some aspects, a container can be a well in a 384-well plate. In some aspects, each composition comprises a cDNA region derived from a single sample. In some aspects, each composition comprises a sample identification-adapter region comprising a sample identification region coupled to an adapter region. In some aspects the sequence of the sample identification region of each sample identification-adapter region in a library is distinct from the nucleotide sequence of the sample identification region of the other sample identification-adapter regions present in each separate container in the library. In some aspects the sample identification-adapter region is attached to the cDNA region. In some aspects the sample identification-adapter region is attached to the cDNA region by binding between their 3' regions. In some aspects the sample identification-adapter region is attached to the cDNA region by G:C binding. In some aspects, the cDNA region comprises an RNA polynucleotide hybridized to a DNA polynucleotide. In some aspects, the cDNA region comprises an mRNA polynucleotide hybridized to a cDNA polynucleotide.

In some aspects, the plurality of polynucleotide compositions in a polynucleotide library can comprise at least 2, at least 3, at least 10, at least 30, at least 100, at least 300, at least 1000, at least 3000, at least 10,000, at least 30,000, at least 100,000, at least 300,000, at least 1,000,000, at least 3,000,000, at least 10,000,000, at least 30,000,000, or more members. In other aspects, the plurality of polynucleotide compositions in a polynucleotide library can comprise at least 2, at least 3, at least 10, at least 30, at least 100, at least 300, at least 1000, at least 3000, at least 10,000, at least 30,000, or more genes of a cell sample's whole transcriptome. In other aspects, the plurality of polynucleotide compositions in a polynucleotide library comprises at least 1, at least 2, at least 3, at least 10, at least 30, at least 100, at least 300, at least 1000, at least 10,000, at least 100,000, at least 1,000,000, at least 10,000,000, at least 1,000,000,000 or more of the different antibody species present in the blood of an individual. These the antibody species can be expressed by plasmablasts, plasma cells, memory B cells, long-lived plasma cells, naïve B cells, other B lineage cells, or combinations thereof.

Vectors

In some aspects, a composition can include a vector. Vectors can be used in the transformation of a host cell with a nucleic acid sequence. In some aspects, a vector can include one or more polynucleotides described herein. In one embodiment, a library of nucleic acid sequences encoding target polypeptides may be introduced into a population of cells, thereby allowing screening of a library. The term "vector" is used to refer to a carrier nucleic acid molecule into which a nucleic acid sequence can be inserted for introduction into a cell where it can be replicated. A nucleic acid sequence can be "exogenous" or "heterologous" which means that it is foreign to the cell into which the vector is being introduced or that the sequence is homologous to a sequence in the cell but in a position within the host cell nucleic acid in which the sequence is ordinarily not found. Vectors include plasmids, cosmids, and viruses (e.g., bacteriophage). One of skill in the art may construct a vector through standard recombinant techniques, which are described in Maniatis et al., 1988 and Ausubel et al., 1994, both of which references are incorporated herein by reference. In some aspects, a vector can be a vector with the constant regions of an antibody pre-engineered in. In this way, one of skill can clone just the VDJ regions of an antibody of interest and clone those regions into the pre-engineered vector.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences for the transcription and possibly translation of an operably linked coding sequence in a particular host organism. In addition to control sequences that govern transcription and translation, vectors and expression vectors may contain nucleic acid sequences that serve other functions as well.

In some aspects, a vector can include a promoter. In some aspects, a vector can include an enhancer. A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (see U.S. Pat. Nos. 4,683,202, 5,928,906, each incorporated herein by reference).

In some aspects, a promoter and/or enhancer that effectively directs the expression of the DNA segment in the cell type chosen for expression. One example of such promoter that may be used is the *E. coli* arabinose or T7 promoter. Those of skill in the art of molecular biology generally are familiar with the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

In some aspects, vectors can include initiation signals and/or internal ribosome binding sites. A specific initiation signal also may be included for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In some aspects, a vector can include sequences that increase or optimize the expression level of the DNA segment encoding the gene of interest. An example of such sequences includes addition of introns in the expressed mRNA (Brinster, R. L. et al. (1988) Introns increase transcriptional efficiency in transgenic mice. Proc. Natl. Acad. Sci. USA 85, 836-40; Choi, T. et al. (1991) A generic intron increases gene expression in transgenic mice. Mol. Cell. Biol. 11, 3070-4). Another example of a method for optimizing expression of the DNA segment is "codon optimization". Codon optimization involves insertion of silent mutations in the DNA segment to reduce the use of rare codons to optimize protein translation (Codon engineering for improved antibody expression in mammalian cells. Carton J M, Sauerwald T, Hawley-Nelson P, Morse B, Peffer N, Beck H, Lu J, Cotty A, Amegadzie B, Sweet R. Protein Expr Purif. 2007 October; 55(2):279-86. Epub 2007 Jun. 16).

In some aspects, a vector can include multiple cloning sites. Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

In some aspects, a vector can include a termination signal. The vectors or constructs will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

Terminators contemplated for use include any known terminator of transcription described herein or known to one of ordinary skill in the art, including but not limited to, for example, rho dependent or rho independent terminators. In certain embodiments, the termination signal may be a lack of transcribable or translatable sequence, such as due to a sequence truncation.

In some aspects, a vector can include an origin of replication.

In order to propagate a vector in a host cell, it may contain one or more origins of replication sites (often termed "ori"), which is a specific nucleic acid sequence at which replication is initiated.

In some aspects, a vector can include one or more selectable and/or screenable markers. In certain embodiments, cells containing a nucleic acid construct may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

In one aspect, the vector can express DNA segments encoding multiple polypeptides of interest. For example, DNA segments encoding both the immunoglobulin heavy chain and light chain can be encoded and expressed by a single vector. In one aspect, both DNA segments can be included on the same expressed RNA and internal ribosome binding site (IRES) sequences used to enable expression of the DNA segments as separate polypeptides (Pinkstaff J K, Chappell S A, Mauro V P, Edelman G M, Krushel L A., Internal initiation of translation of five dendritically localized neuronal mRNAs., Proc Natl Acad Sci USA. 2001 Feb. 27; 98(5):2770-5. Epub 2001 Feb. 20). In another aspect, each DNA segment has its own promoter region resulting in expression of separate mRNAs (Andersen C R, Nielsen L S, Baer A, Tolstrup A B, Weilguny D. Efficient Expression from One CMV Enhancer Controlling Two Core Promoters. Mol Biotechnol. 2010 Nov. 27. [Epub ahead of print]).

Host Cells and Expression Systems

In some aspects, a composition can include a host cell. In some aspects, a host cell can include a polynucleotide or vector described herein. In some aspects, a host cell can include a eukaryotic cell (e.g., insect, yeast, or mammalian) or a prokaryotic cell (e.g., bacteria). In the context of expressing a heterologous nucleic acid sequence, "host cell" can refer to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular embodiments, a host cell is a Gram negative bacterial cell. These bacteria are suited for use in that they possess a periplasmic space between the inner and outer membrane and, particularly, the aforementioned inner membrane between the periplasm and cytoplasm, which is also known as the cytoplasmic membrane. As such, any other cell with such a periplasmic space could be used. Examples of Gram negative bacteria include, but are not limited to, *E. coli, Pseudomonas aeruginosa, Vibrio cholera, Salmonella typhimurium, Shigella flexneri, Haemophilus influenza, Bordotella pertussi, Erwinia amylovora, Rhizobium* sp. The Gram negative bacterial cell may be still further defined as bacterial cell which has been transformed with the coding sequence of a fusion polypeptide comprising a candidate binding polypeptide capable of binding a selected ligand. The polypeptide is anchored to the outer face of the cytoplasmic membrane, facing the periplasmic space, and may comprise an antibody coding sequence or another sequence. One means for expression of the polypeptide is by attaching a leader sequence to the polypeptide capable of causing such directing.

Numerous prokaryotic cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5-alpha, JM109, and KCB, as well as a number of commercially available bacterial hosts such as SURE™ Competent Cells and SOLOPACK™ Gold Cells (STRATAGENE™, La Jolla). In some aspects, other bacterial cells such as *E. coli* LE392 are contemplated for use as host cells.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

In some aspects, a host cell is mammalian. Examples include CHO cells, CHO-K1 cells, or CHO-S cells. Other mammalian host cells include NSO cells and CHO cells that are dhfr-, e.g., CHO-dhfr-, DUKX-B11 CHO cells, and DG44 CHO cells.

Numerous expression systems exist can that comprise at least a part or all of the compositions disclosed herein. Expression systems can include eukaryotic expression systems and prokaryotic expression systems. Such systems could be used, for example, for the production of a polypeptide product identified as capable of binding a particular ligand. Prokaryote-based systems can be employed to produce nucleic acid sequences, or their cognate polypeptides, proteins and peptides. Many such systems are commercially and widely available. Other examples of expression systems comprise of vectors containing a strong prokaryotic promoter such as T7, Tac, Trc, BAD, lambda pL, Tetracycline or Lac promoters, the pET Expression System and an *E. coli* expression system.

Polypeptides

In some aspects, a composition can include a polypeptide. In some aspects, a polypeptide encoded by a polynucleotide described herein can be expressed, e.g., from a host cell. The terms "polypeptide" or "protein" include a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" encompass antigen binding proteins, antibodies, or sequences that have deletions from, additions to, and/or substitutions of one or more amino acids of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a binding antibody, useful fragments include but are not limited to a CDR region, a variable domain of a heavy and/or light chain, a portion of an antibody chain or just its variable region including two CDRs, and the like.

The term "isolated protein" means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, nucleic acids of synthetic origin, or any combination thereof can encode such an isolated protein. Preferably, the isolated protein is substantially free from proteins or polypeptides or other contaminants that are found in its natural environment that would interfere with its therapeutic, diagnostic, prophylactic, research or other use.

In some aspects, a polypeptide can include an antigen binding protein (ABP). An "antigen binding protein" ("ABP") as used herein means any protein that binds a specified target antigen. "Antigen binding protein" includes but is not limited to antibodies and binding parts thereof, such as immunologically functional fragments. Peptibodies are another example of antigen binding proteins. The term "immunologically functional fragment" (or simply "fragment") of an antibody or immunoglobulin chain (heavy or light chain) antigen binding protein, as used herein, is a species of antigen binding protein comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding proteins, including intact antibodies, for binding to a given epitope. In some embodiments, the fragments are neutralizing fragments. These biologically active fragments can be produced by recombinant DNA techniques, or can be produced by enzymatic or chemical cleavage of antigen binding proteins, including intact antibodies. Immunologically functional immunoglobulin fragments include, but are not limited to, Fab, a diabody (heavy chain variable domain on the same polypeptide as a light chain variable domain, connected via a short peptide linker that is too short to permit pairing between the two domains on the same chain), Fab', F(ab')2, Fv, domain antibodies and single-chain antibodies, and can be derived from any mammalian source, including but not limited to human, mouse, rat, camelid or rabbit. It is further contemplated that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life. As will be appreciated by one of skill in the art, an antigen binding protein can include nonprotein components. Additional details about antigen binding proteins and antibodies such as modifications, variants, methods of making, and methods of screening can be found in U.S. Pat. Pub. 20110027287, herein incorporated by reference in its entirety for all purposes.

In some aspects, a polypeptide can include an antibody. The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

A therapeutically effective amount of an ABP can be administered to a subject in need thereof. ABPs can be formulated in pharmaceutical compositions. These compositions can comprise, in addition to one or more of the ABPs, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

ABP administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

Immune Cells

A sample can include immune cells. The immune cells can include T cells and B cells. T-cells (T lymphocytes) include, for example, cells that express T cell receptors. B-cells include, for example, activated B cells, blasting B cells, plasma cells, plasmablasts, memory B cells, B1 cells, B2 cells, marginal-zone B cells, and follicular B cells. T cells include activated T cells, blasting T cells, Helper T cells (effector T cells or Th cells), cytotoxic T cells (CTLs), memory T cells, central memory T cells, effector memory T cells and regulatory T cells. A sample can include a single cell in some applications (e.g., a calibration test to define relevant T or B cells) or more generally at least 1,000, at least 10,000, at least 100,000, at least 250,000, at least 500,000, at least 750,000, or at least 1,000,000 cells.

B Cells

As used herein a "B cell" refers to any cell that has at least one rearranged immunoglobulin gene locus. A B cell can include at least one rearranged immunoglobulin heavy chain locus or at least one rearranged immunoglobulin light chain locus. A B cell can include at least one rearranged immunoglobulin heavy chain locus and at least one rearranged immunoglobulin light chain locus. B cells are lymphocytes that are part of the adaptive immune system. B cells can include any cells that express antibodies either in the membrane-bound form as the B-cell receptor (BCR) on the cell surface or as secreted antibodies. B cells can express immunoglobulins (antibodies, B cell receptor). Antibodies can include heterodimers formed from the heavy and light immunoglobulin chains. The heavy chain is formed from gene rearrangements of the variable, diversity, and junctional (VDJ) genes to form the variable region, which is joined to the constant region. The light chain is formed from gene rearrangements of the variable and junctional (VJ) genes to form the variable region, which is then joined to the constant region. Owing to a large possible number of junctional combinations, the variable regions of the antibody gene (which is also the BCR) have huge diversity, enabling B cells to recognize any foreign antigen and mount a response against it.

B-Cell Activation and Differentiation

B cells are activated and differentiate when they recognize an antigen in the context of an inflammatory immune response. They usually include 2 signals to become activated, one signal delivered through BCR (a membrane-bound form of the rearranged immunoglobulin), and another delivered through CD40 or another co-stimulatory molecule. This second signal can be provided through interaction with helper T cells, which express the ligand for CD40 (CD40L) on their surface. B cells then proliferate and may undergo somatic hypermutation, where random changes in the nucleotide sequences of the antibody genes are made, and B cells whose antibodies have a higher affinity B cells are selected. They may also undergo "class-switching", in which the constant region of the heavy chain encoding the IgM isotype is switched to the constant region encoding the IgG, IgA, or IgE isotype. Differentiating B cells may end up as memory B cells, which are usually of higher affinity and classed switched, though some memory B cells are still of the IgM isotype. Memory B cells can also become activated and differentiate into plasmablasts and ultimately, into plasma cells. Differentiating B cells may also first become plasmablasts, which then differentiate to become plasma cells.

Affinity Maturation and Clonal Families

A clonal family is generally defined by the use of related immunoglobulin heavy chain and/or light chain V(D)J sequences by 2 or more samples. Related immunoglobulin heavy chain V(D)J sequences can be identified by their shared usage of V(D)J gene segments encoded in the genome. Within a clonal family there are generally subfamilies that vary based on shared mutations within their V(D)J segments, that can arise during B cell gene recombination and somatic hypermutation.

Activated B cells migrate and form germinal centers within lymphoid or other tissues, where they undergo affinity maturation. B cells may also undergo affinity maturation outside of germinal centers. During affinity maturation, B cells undergo random mutations in their antibody genes, concentrated in the complementary determining regions (CDRs) of the genes, which encode the parts of the antibody that directly bind to and recognize the target antigen against which the B cell was activated. This creates sub-clones from the original proliferating B cell that express immunoglobulins that are slightly different from the original clone and from each other. Clones compete for antigen and the higher-affinity clones are selected, while the lower-affinity clones die by apoptosis. This process results in the "affinity maturation" of B cells and consequently in the generation of B cells expressing immunoglobulins that bind to the antigen with higher affinity. All the B cells that originate from the same 'parent' B cell form clonal families, and these clonal families include B cells that recognize the same or similar antigenic epitopes. In some aspects, we expect that clones present at higher frequencies represent clones that bind to antigen with higher affinity, because the highest-affinity clones are selected during affinity maturation. In some aspects, clones with different V(D)J segment usage exhibit different binding characteristics. In some aspects, clones with the same V(D)J segment usage but different mutations exhibit different binding characteristics.

Memory B Cells

Memory B cells are usually affinity-matured B cells, and may be class-switched. These are cells that can respond more rapidly to a subsequent antigenic challenge, significantly reducing the time included for affinity-matured antibody secretion against the antigen from ~14 days in a naive organism to ~7 days.

Plasmablasts and Plasma Cells

Plasma cells can be either long-lived or short-lived. Long-lived plasma cells may survive for the lifetime of the organism, whereas short-lived plasma cells can last for 3-4 days. Long-lived plasma cells reside either in areas of inflammation, in the mucosal areas (in the case of IgA-secreting plasma cells), in secondary lymphoid tissues (such as the spleen or lymph nodes), or in the bone marrow. To reach these divergent areas, plasmablasts fated to become long-lived plasma cells may first travel through the bloodstream before utilizing various chemokine gradients to traffic to the appropriate areas. Plasmablasts are cells that are affinity matured, are typically classed-switched, and usually secrete antibodies, though generally in lower quantities than the quantity of antibody produced by plasma cells. Plasma cells are dedicated antibody secretors.

Characteristics of TCR and BCR Genes

Since identifying recombinations are present in the DNA of each individual adaptive immune cell as well as their associated RNA transcripts, either RNA or DNA can be sequenced. A recombed sequence from a T-cell or B-cell can also be referred to as a clonotype. The DNA or RNA can correspond to sequences from T-cell receptor (TCR) genes or immunoglobulin (Ig) genes that encode antibodies. For example, the DNA and RNA can correspond to sequences encoding alpha, beta, gamma, or delta chains of a TCR. In a majority of T-cells, the TCR is a heterodimer consisting of an alpha-chain and beta-chain. The TCR-alpha chain is generated by VJ recombination, and the beta chain receptor is generated by V(D)J recombination. For the TCR-beta chain, in humans there are 48 V segments, 2 D segments, and 13 J segments. Several bases may be deleted and others added (called N and P nucleotides) at each of the two junctions. In a minority of T-cells, the TCRs consist of gamma and delta chains. The TCR gamma chain is generated by VJ recombination, and the TCR delta chain is generated by V(D)J recombination (Kenneth Murphy, Paul Travers, and Mark Walport, Janeway's Immunology 7th edition, Garland Science, 2007, which is herein incorporated by reference in its entirety).

The DNA and RNA analyzed in the methods can correspond to sequences encoding heavy chain immunoglobulins (IgH) with constant regions (alpha, delta, gamma, epsilon, or mu) or light chain immunoglobulins (IgK or IgL) with constant regions lambda or kappa. Each antibody can have two identical light chains and two identical heavy chains. Each chain is composed of a constant (C) and a variable region. For the heavy chain, the variable region is composed of a variable (V), diversity (D), and joining (J) segments. Several distinct sequences coding for each type of these segments are present in the genome. A specific VDJ recombination event occurs during the development of a B-cell, marking that cell to generate a specific heavy chain. Diversity in the light chain is generated in a similar fashion except that there is no D region so there is only VJ recombination. Somatic mutation often occurs close to the site of the recombination, causing the addition or deletion of several nucleotides, further increasing the diversity of heavy and light chains generated by B-cells. The possible diversity of the antibodies generated by a B-cell is then the product of the different heavy and light chains. The variable regions of the heavy and light chains contribute to form the antigen recognition (or binding) region or site. Added to this diversity is a process of somatic hypermutation which can occur after a specific response is mounted against some epitope. In this process mutations occur in those B-cells that are able to recognize the specific epitope leading to greater diversity in antibodies that may be able to bind the specific epitope more strongly. All these factors contribute to great diversity of antibodies generated by the B-cells. Many billions and maybe more than a trillion distinct antibodies may be generated. The basic premise for generating T-cell diversity is similar to that for generating antibodies by B-cells. An element of T-cell and B-cell activation is their binding to epitopes. The activation of a specific cell leads to the production of more of the same type of cells leading to a clonal expansion.

Complementarity determining regions (CDR), or hypervariable regions, are sequences in the variable domains of antigen receptors (e.g., T cell receptor and immunoglobulin) that can bind an antigen. The chain of each antigen receptor contains three CDRs (CDR1, CDR2, and CDR3). The two polypeptides making T cells (alpha and beta) and immunoglobulin (IgH and IgK or IgL) contribute to the formation of the three CDRs.

The part of CDR1 and CDR2 that is coded for by TCR-beta lies within one of 47 functional V segments. Most of the diversity of CDRs is found in CDR3, with the diversity being generated by somatic recombination events during the development of T lymphocytes.

A great diversity of BCR is present inter and intra-individuals. The BCR is composed of two genes IgH and IgK (or IgL) coding for antibody heavy and light chains. Three Complementarity Determining Region (CDR) sequences that bind antigens and MHC molecules have the most diversity in IgH and IgK (or IgL). The part of CDR1 and CDR2 coded for by IgH lies within one of 44 functional V segments. Most of the diversity in naive B cells emerges in the generation of CDR3 through somatic recombination events during the development of B lymphocytes. The recombination can generate a molecule with one of each of the V, D, and J segments. In humans, there are 44 V, 27 D, and 6 J segments; thus, there is a theoretical possibility of more than 7,000 combinations. In a small fraction of BCRs (about 5%) two D segments are found. Furthermore, several bases may be deleted and others added (called N and P nucleotides) at each of the two junctions generating a great degree of diversity. After B cell activation a process of affinity maturation through somatic hypermutation occurs. In this process progeny cells of the activated B cells accumulate distinct somatic mutations throughout the gene with higher mutation concentration in the CDR regions leading to generating antibodies with higher affinity to the antigens. In addition to somatic hypermutation activated B cells undergo the process of isotype switching. Antibodies with the same variable segments can have different forms (isotypes) depending on the constant segment. Whereas all naive B cells express IgM (or IgD), activated B cells mostly express IgG but also IgM, IgA and IgE. This expression switching from IgM (and/or IgD) to IgG, IgA, or IgE occurs through a recombination event causing one cell to specialize in producing a specific isotype. There is one segment for each IgM, IgD, and IgE, two segments for IgA, and four segments for IgG.

Computer Implementation

In some aspects, one or more methods described herein can be implemented on a computer. In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

Kits

A kit can include a polynucleotide, a polynucleotide library, a vector, and/or a host cell disclosed herein and instructions for use. The kits may comprise, in a suitable container, a polynucleotide, a polynucleotide library, a vector, and/or a host cell disclosed herein, one or more controls, and various buffers, reagents, enzymes and other standard ingredients well known in the art.

The container can include at least one well on a plate comprising one or more wells. The container can include at least one vial, test tube, flask, bottle, syringe, or other container means, into which a polynucleotide, a polynucleotide library, a vector, and/or a host cell may be placed, and in some instances, suitably aliquoted. Where an additional component is provided, the kit can contain additional containers into which this component may be placed. The kits can also include a means for containing the polynucleotide, a polynucleotide library, a vector, and/or a host cell and any other reagent containers in close confinement for commercial sale. Such containers may include injection or blow-molded plastic containers into which the desired vials are retained. Containers can include labeling with instructions for use and/or warnings.

EXAMPLES

The examples are offered for illustrative purposes only, and are not intended to limit the scope of any embodiment of the present invention in any way. Efforts have been made to ensure accuracy with respect to numbers used (e.g., amounts, temperatures, etc.), but some experimental error and deviation should, of course, be allowed for.

Various methods can employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B(1992); *Current Protocols in Molecular Biology* (2002-; Wiley; Online ISBN: 9780471142720; DOI: 10.1002/04711142727); *Current Protocols in Immunology* (2001-; Wiley; Online ISBN: 9780471142737; DOI: 10.1002/0471142735).

Example 1: Antibody Display Systems and Fully Sequenced, Barcoded Antibody Repertoires PCT/US2012/000221 (filed Apr. 27, 2012) and PCT/US2012/053698 (filed Sep. 4, 2012) describe production of antibody repertoires from individual B-cells through a series of steps beginning with sorting single cells into individual wells followed by lysis, first strand synthesis of cDNA, PCR amplification, and finally next generation sequencing (NGS) of the linear PCR products. During this process proprietary identification regions (i.e., bar codes) are introduced onto the products such that cDNA encoding H+L chains originating from single cells are labeled as pairs. The net result is a pool of cDNA in which cDNA from any given cell has been labeled with the exact same bar code which is unique and distinct from every other barcode incorporated into the cDNA from every other cell isolated using the described methodology.

To date several antibody display systems have been described in the literature including: phage display, ribosome display, mRNA display, and yeast cell display (Hoogenboom 2005). All antibody display technologies share the characteristic of physically linking coding domain sequences with the encoded protein which is then allowed to bind to immobilized antigen or other target binding protein. Particles that are capable of forming stable interactions with target proteins can then be selected from large pools of non-binders. Here phage display will be used as an example with the expectation that the principles used for this approach could easily applied to other display strategies.

Typically phage display systems utilize filamentous bacteriophage such as M13, which includes single stranded DNA encapsulated by a protein sheath. Antibody fragments, encoded by cDNA inserted into the phage genome, are displayed at the surface of the phage particle as fusions with the carboxy-terminus of the minor coat protein pIII. The most commonly used antibody fragment expression formats are single-chain variable fragment (ScFv) and antigen binding fragment (Fab) (for review see Hoogenboom 2005). Additional formats exist that can also be used.

Once the desired antibody format is chosen, the appropriate phagemid vector is purchased or designed and synthesized. To begin the construction of the phagemid library, heavy and light variable regions are amplified from the repertoire. Design and use of 5' and 3' variable region PCR primers is a first step and typically involves the use of species-specific degenerate primer libraries. Primer libraries whose sequences are published have been designed to prime a wide array of possible variable regions. However, since repertoires whose variable sequences have been fully characterized and barcoded are used, alignments are performed with repertoire sequences and those of the primer library. Here alignments are analyzed manually and/or using algorithms designed to select against pairings containing primer:template mismatches concentrated in the 3' end of the primer since these primers would typically have a decreased probability of annealing or being extended. Using this method, it is typical to find a significant number of antibody clones that would not be amplified. These sequences are identified, aligned, and a parsimonious set of custom primers is designed to ensure that as much of the repertoire will be amplified as possible. Additional sequence is added at the 5' ends to accommodate downstream cloning strategies. Alternatively, gene synthesis can be used to generate appropriate heavy chain and light chain sequences for a phagemid library.

Example 2: Combinatorial Library Construction

Cloning strategies to introduce the antibody repetoire into the phagemid vector system will depend on both the antibody format used and the vector that the heavy and light chain fragments are being ligated into. For an scFv phage library, a cDNA encoding a fusion of light chain variable region, linker (typically $(Gly_4Ser)_n$), heavy chain variable region, and gIII c-terminus can be constructed. For Fab libraries, two cistrons expressed from the same promoter are created, typically including the light chain variable region and the heavy chain variable region fused to the c-terminus of gIII. For either scFv or Fab libraries, a number of cloning strategies can be used to generate display libraries. In one strategy, heavy and light chains can be brought together using assembly PCR (Benhar 2002) and then ligated into an appropriate vector. Alternatively, heavy and light chains can be ligated directly into the phagemid vector either sequentially or concurrently. Another method is to use recombination (e.g. Cre-Lox) to introduce the fragment encoding the second chain into a phagemid construct already containing the first chain or vice-versa. In some aspects, the barcodes themselves do not become part of the display library. In some aspects, the operative pairing of chains via barcodes is not necessarily maintained in making the display library.

Example 3: Directed Pair Library Construction

A drawback of traditional combinatorial display libraries is that heavy and light chain pairing is random. This in turn leads to libraries that are much larger and more complex than is necessary, increasing the number of clones that must be screened and potentially increasing the background. For example if the starting material has a complexity of $10^3$ for heavy chains and $10^4$ for light chains then the total complexity of the phage library (assuming no losses or bias during PCR, ligation, or transformation) would be $10^7$. Thus if one wanted to achieve 99% probability that all clones had been screened during a panning step, approximately $10^9$ phagemid would have to be panned.

If the phage library was restricted to only native pairings then the complexity would be $10^4$ to $10^5$, approximately 100 to 1000-fold less compared with random pairings. Since the heavy and light chain pairing is known for the antibody repertoires, it is possible to direct the pairing of antibodies during phage library construction in a more specific fashion. One way to do this would be to create "sub-libraries" of the repertoire in which smaller pools of heavy and light chain variable regions are used during the H+L chain linking step in the cloning process. These pools of heavy and light chain material can be generated by increasing the number of primer-specific PCR reactions for both chains and then pairing the products according to the paired sequence information from the antibody repertoire. While not achieving perfect native pairing, this method would significantly reduce the complexity of the resulting phagemid library. For example, a repertoire with a complexity of $10^3$ for both heavy and light chains would be expected to give a phagemid library of $10^6$ complexity using a traditional combinatorial approach. If the library was segmented into 15 pools of 100 H+L chains in which specific pairings were enriched, then the resulting complexity would be $100^2 \times 15$ or $1.5 \times 10^5$, almost ten-fold less than a random combinatorial library.

Other methods can be used to achieve nearly exclusive native pairing. One method would be to use the barcode sequence identity contained in H+L chains originating from the same cell in assembly PCR. Within a heterogenous pool of H+L chain cDNA, complimentary strands of H+L cDNA from the same cell would anneal in their barcode regions and would effectively become physically joined in the assembly PCR reaction. Once coupled, this pool of specifically linked cDNA would then be inserted into a phagemid vector. Alternatively, assembly PCR could be performed before the cDNA from individual cells is pooled (Dekosky 2013) and the resulting material inserted into the phagemid vector.

Example 4: Panning and Repetoire Annotation

Once the cloning steps are completed, the vector is then transformed into bacteria, phagemid produced, amplified, and titered (Benhar 2002). Aliquots of the final phagemid library can then be analyzed using NGS to ensure that the original antibody repertoire is faithfully represented. Once this is confirmed, the library can then be "panned" against an antigen using one or more methods. Essentially these methods include antigen that can, in a variety of ways, be washed such that phagemid which do not bind antigen are removed while those that do bind remain. Bound phagemid are then recovered, used to re-infect host bacteria, and amplified. The process can then be repeated to enhance enrichment for true binders.

A number of panning strategies can be employed (Hoogenboom 2005) and include but are not limited to:
  i. Recombinant protein: Can be immobilized non-specifically to a solid substrate such as plastic, covalently cross-linked to an activated-substrate; biotinylated and then bound to a streptavidin-coated substrate before or after incubation with phagemid.
  ii. Cells: whole cells displaying antigen in a native state or transfected cells (stable or transient) expressing a recombinant antigen. Using this method it is also possible to select for antigens/phagemid that are internalized following binding.
  iii. Subcellular fractions.
  iv. Bacteria, fungi or protozoa.
  v. Isolated tissue.
  vi. In-vivo recovery of tissue(s) from animals injected with phagemid.

Figure 1:
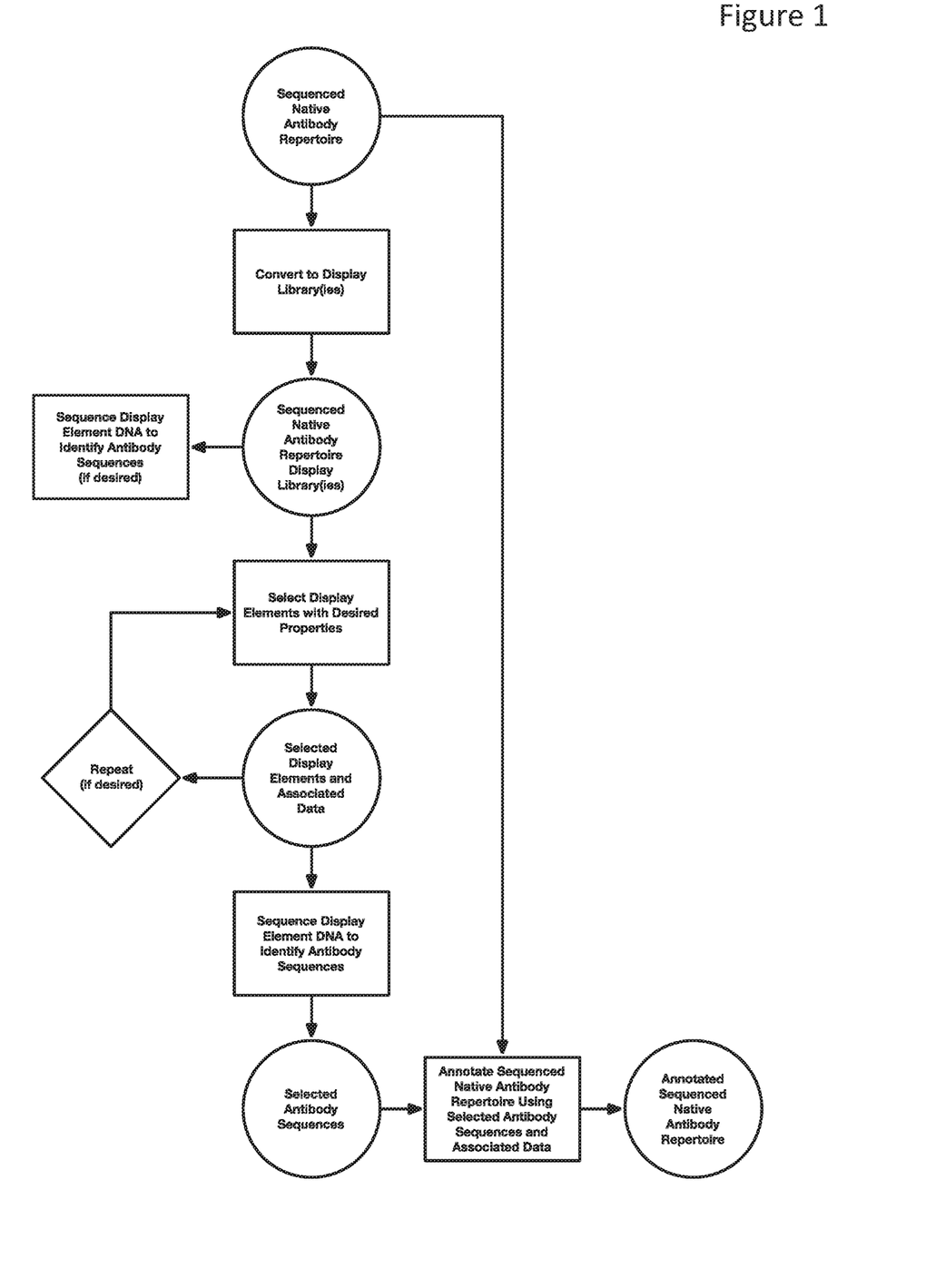
FIG. 1 shows an embodiment of using nanoexpression to interrogate antigen specificity within one or more antibody repertoires. This figure encompasses methods, compositions, and systems.

Typically phagemid isolated from the first round of panning are re-panned at least once, with several rounds of panning performed in total. This can be done by repeating the method and conditions performed in the first round. Alternatively other methods listed above can be used. Binding and/or washing stringency (e.g. increasing salt concentration and/or use of chaotropic agents) can be increased to filter out false positives and enrich for higher affinity binders. One can enrich for binders with very short "on-rates" by adding unbound soluble antigen after only a brief incubation with phagemid and immobilized antigen. Similarly, phagemid with long "off-rates" can be selected by additional washes following extended incubations. Phagemid clones positive for binding are sequenced after each panning step and analyzed by ELISA or other assays useful for assessing binding, affinity, etc. Once panning is completed, isolated phage clones are sequenced by NGS. In addition, phagemid that do not bind in each round of panning (i.e. are washed off) are recovered, inserts amplified by PCR and sequenced using NGS. (Zhou 2012, Hoen 2012, Zhang 2011, Ravn 2013, Beerli 2010) The phylogenetic tree from the starting repertoire is then annotated for binding and potency data from ELISA assays or other assays. Annotation includes combining the original sequences or sequence data with data coming from manipulating or binding the display library/system, and includes additional sequence data, binding data, functional assay data, element abundance data, and display library composition data (both protein and nucleic acid) data. Individual clones of interest can then be chosen for expression as full length immunoglobulins in eukaryotic expression systems for further analysis and characterization. One embodiment of the described methodology is shown in FIG. 1.

Figure 2:
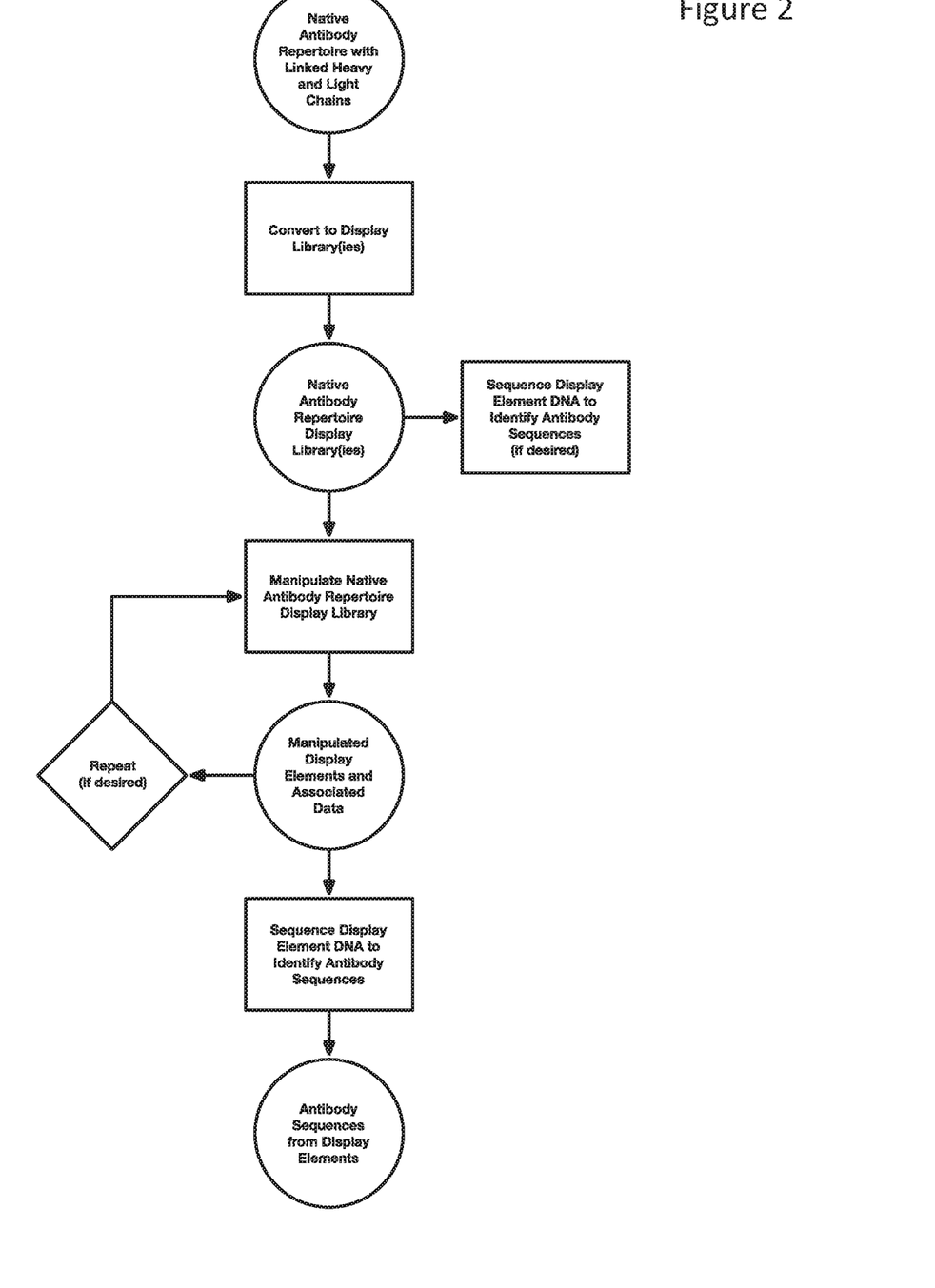
FIG. 2 shows an embodiment of using nanoexpression to interrogate antigen specificity within one or more antibody repertoires. This figure encompasses methods, compositions, and systems.

Example 5: Use of Linked Heavy and Light Chain Sequences for Library Construction and Panning In some aspects, a native antibody repertoire with operatively or physically linked heavy and light chains can be used for display system construction ("linking-PCR"). Such as system can involve the following steps: A. Obtain an antibody repertoire (e.g., a native antibody repertoire) with operatively or physically linked heavy and light chain sequences or sequence data; B. Convert the sequences or data to a display library; C. Perform manipulation of the display library; and D. Sequence the manipulated display library or elements to obtain information about the elements of the display library. See FIG. 2.

In some aspects of the "linking-PCR" approach the heavy and light chain sequences are physically linked. In this case, the repertoire may not necessarily be sequenced before making the display library. In some aspects, the "linking-PCR" approach includes having barcodes present in the antibody repertoire, regardless of whether it is generated via "operative" or "physical" linking. However, having barcodes is not necessary if the chains are physically linked. In some aspects, the repertoire can include at least 10, 25, 50, 100, 250, 500, 1000, or 10,000 linked native heavy and light chain pairs. In some aspects, the "linking-PCR" approach can include introducing or not introducing mutations after conversion of the repertoire to a display library.

REFERENCES

Benhar 2002. Phage display of single chain antibody constructs. Current Protocols in Immunology 10.19B.1. 2002.
DeKosky 2013. High-throughput sequencing of the paired human immunoglobulin heavy and light chain repertoire. *Nature Biotechnology* 31:166-169. 2013
Hoogenboom 2005. Selecting and screening recombinant antibody libraries. Nature Biotechnology 23(9): 1105.
Stemmer 1995 Single-step assembly of a gene and entire plasmid from large numbers of oligodeoxyribonucleotides. Gene 164 (1):49-53
Willats 2002. Phage display: practicalities and prospects. *Plant Molecular Biology* 50: 837-854, 2002.
Zhou 2012. Selection and characterization of cell binding and internalizing phage antibodies. Archives of Biochemistry and Biophysics 526 (2012) 107-113.
Hoen 2012. Phage display screening without repetitious selection rounds. Analytical Biochemistry 421 (2012) 622-631.
Zhang 2011. Phenotype-information-phenotype cycle for deconvolution of combinatorial antibody libraries selected against complex systems. PNAS. 108(33) 13456-61.
Ravn 2013. Deep sequencing of phage display libraries to support antibody discovery. Methods (2013) 99-110.
Beerli 2010. Mining human antibody repertoires. mAbs 2:4, 365-378, July-August 2010.

The invention claimed is:

1. A method of annotating an antibody display system library with binding data, comprising:
   obtaining an antibody display system library comprising a plurality of recombinant nucleic acid sequences encoding antigen binding proteins comprising heavy and light chain variable regions, wherein the antibody display system comprises phage display, ribosome display, mRNA display, or yeast cell display;
   binding the antibody display system library to an antigen;
   determining a dataset comprising binding data and sequence data for the library, wherein the binding data is determined using an ELISA assay;
   wherein the sequence data comprises native pairs of heavy and light chain antibody sequences from a single activated B cell;
   and annotating the library with the binding and sequence data.

2. The method of claim 1, wherein the binding data is affinity data.

3. The method of claim 1, wherein the binding data is antigen-specificity data.

4. The method of claim 1, wherein the antigen is a recombinant protein, a cell, a subcellular fraction, a bacterium, fungi, protozoa, or a tissue.

5. The method of claim 1, wherein the sequence data is determined using sequencing.

6. The method of claim 1, wherein the sequence data is determined using next generation sequencing (NGS).

7. A method of annotating an antibody display system library with binding data, comprising:
   obtaining an antibody display system library comprising a plurality of recombinant nucleic acid sequences encoding antigen binding proteins comprising heavy and light chain variable regions, wherein the antibody display system comprises phage display, ribosome display, mRNA display, or yeast cell display;
   binding the antibody display system library to an antigen;
   determining a dataset comprising binding data and sequence data for the library;
   wherein the binding data is antigen-specificity data determined by panning the antibody display system library to enrich for bound antigen binding proteins and determining the sequences of the bound antigen binding proteins;

wherein the sequence data comprises native pairs of heavy and light chain variable region sequences, each of the native pairs from a single activated B cell;

and annotating the library with the binding and sequence data.

* * * * *